United States Patent
Hall

(12) 
(10) Patent No.: US 6,634,315 B1
(45) Date of Patent: Oct. 21, 2003

(54) METHOD OF FEEDING ANTS AND A FOOD DISPENSER FOR THE PURPOSE

(76) Inventor: Kjell Hall, Skorstensvägen 46, 393 63 Kalmar (SE)

( * ) Notice: Subject to any disclaimer, the term of this patent is extended or adjusted under 35 U.S.C. 154(b) by 0 days.

(21) Appl. No.: 09/980,316

(22) PCT Filed: May 29, 2000

(86) PCT No.: PCT/SE00/01095

§ 371 (c)(1), (2), (4) Date: Nov. 26, 2001

(87) PCT Pub. No.: WO00/72671

PCT Pub. Date: Dec. 7, 2000

(30) Foreign Application Priority Data

May 31, 1999 (SE) .............................................. 9901977

(51) Int. Cl.$^7$ ............................. E04B 1/72; A01K 67/00
(52) U.S. Cl. ........................................ 119/6.5; 52/101
(58) Field of Search ............................. 119/6.5; 43/131; 52/101

(56) References Cited

U.S. PATENT DOCUMENTS

| 716,533 | A | * | 12/1902 | Harker | 43/131 |
|---|---|---|---|---|---|
| 948,805 | A | | 2/1910 | Akerlind | |
| 1,922,702 | A | * | 8/1933 | Kristman | 43/131 |
| 4,441,272 | A | | 4/1984 | Bartz | 43/1 |
| 5,398,642 | A | | 3/1995 | Harwich | 119/6.5 |
| 5,619,952 | A | * | 4/1997 | Walker | 119/61 |

FOREIGN PATENT DOCUMENTS

| EP | 0204999 | 1/2000 |
|---|---|---|
| GB | 2305843 | 4/1997 |
| JP | 9131154 | 11/1995 |
| SE | 468155 | 6/1937 |
| WO | WO 96/32009 | 10/1996 |

* cited by examiner

*Primary Examiner*—Robert P. Swiatek

(57) ABSTRACT

A method for preventing the invasion of dwelling houses etc by ants, by luring the ants to locations near the house, where food is provided for them. The food dispenser consists of a round body which contains a floor section which holds an ant food.

4 Claims, 1 Drawing Sheet

METHOD OF FEEDING ANTS AND A FOOD DISPENSER FOR THE PURPOSE

The present invention relates to a method for preventing ants from entering a dwelling house or similar building. The invention also relates to a food dispenser for use in implementing this method.

TECHNICAL BASIS

Ants can cause human beings problems of several kinds. On the one hand there is Camponotus—the carpenter ant—a pest which attacks wood, and on the other is the much milder yellow ant, particularly the black variety—Lasius niger—commonly known as the black ant. In recent years the very unpleasant Pharaoh ant—Monomorium pharaonis—has spread to some countries in the northern hemisphere. This insect can be a real nuisance to humanity if it establishes itself in an apartment building, a laundry, bakery or hospital for example, and it consumes food-stuffs of all kinds. It can even attack wound scabs under the bandages of hospital patients. Its colonies are usually strong in numbers, and are difficult to combat.

The black ant is one of our most common ants. It invades many houses during a few weeks of spring each year—the so-called ant season, in search of food, before its natural supplies of nourishment have become available. These are mainly sweet materials such as the sugar-rich secretions of the greenfly, so-called honeydew. In our houses the ants hope to find sugar, juices, sweet drinks, cake crumbs etc. Black ants should therefore be regarded simply as an unhygienic nuisance, while carpenter ants and termites are recognized as pests, and Pharaoh ants are vermin, and have unpleasant habits.

In the past, the removal of carpenter, Pharaoh, and black ants from buildings, mainly dwelling houses, has had to be done by extermination, often using dangerous chemicals or poisons, with the attendant risk of these affecting the natural surroundings. In addition, these methods of killing constitute cruelty to animals, and they conflict with today's enlightened views on this subject.

THE OBJECT OF THE INVENTION

The object of the invention is therefore to provide a method and a food dispenser of the kind mentioned in the introduction, by means of which ants can be prevented from invading a building, without the use of cruelty or pesticides and without extermination. This end is achieved using the method and food dispenser in accordance with the invention, as specified in claims 1 and 4. Further development of the invention is explained in the dependent claims.

DESCRIPTION OF THE INVENTION

The invention is based upon entomological studies of ants, which show that certain ants, especially colonies of black ants, are hostile to other ant colonies. It has been clearly demonstrated that black ants and carpenter ants are enemies. Carpenter ants, which are considered to have a phlegmatic temperament, defend themselves when hard pressed but soon retreat even for an inferior enemy force. The black ant is smaller in size but is much more aggressive, and defends its territory fiercely against carpenter ants. The black ant should also be capable of defending itself successfully against Pharaoh ants and termites, even though research results are not completely unanimous on this point. Ants in general, according to the literature available, are termites' worst enemies.

The basic idea of the invention is to attract a colony of black ants, without the use of any kind of poison, to one or more chosen locations close to the building which is to be protected. The presence of the black ants in chosen places outside the building will deter any other, more troublesome ants and termites which may approach the area. The invention will thus keep the building free from black ants, which will in turn ensure its protection against carpenter and Pharaoh ants and termites. It can therefore be said that the invention makes use of black ants as a form of biological protection.

The biological control of vermin or noxious insects with the aid of other, more useful, insects is not in itself a new idea; e.g. see U.S. Pat. No. 4,441,272, GB 2.305.843 and EP 0204 999. However, biological protection of this kind has never yet been used or even proposed for the purpose of preventing the ingress of ants into dwelling houses or other buildings; the use of environmentally-dangerous and poisonous chemicals has hitherto been the universal method of combating such undesirable invasions of ants.

Furthermore, it is intended that any black ants already present in the house will be lured outside by the use of a harmless bait, and will be attracted to stay within the chosen areas by special food dispensers designed to be replenished during the whole so-called ant season, and to provide the ants with nourishment while other food sources are lacking.

The provision of life-sustaining food for ants is not in itself a new idea, but has long been used in connection with entomological studies of ants in a so-called formicarier, a kind of artifical dwelling for the insects; they are not held in captivity but are free to enter and leave the unit, which is the subject of patent specification U.S. Pat. No. 5,398,642, and which is intended only for studying ants. Patent specification U.S. Pat. No. 5,398,642 does not deal with problems arising from ants or termites in dwellings nor with the placing of a formicarier near a building for this purpose. The complicated construction of the formicarier, with only a few small entrances for the ants, makes it unsuitable for use as a food dispenser in the way envisaged with the present invention, which has very open and easy-to-use entrance and exit passages, intended to retain the interest of an entire ant colony, and to effectively lure it out from the building which is to be freed from the attentions of the ants or termites. The food dispenser in this invention is specially designed to allow the ants easy access to the food. Tests carried out over several years with the invention, during the spring period when ants are normally most troublesome, have shown its effectiveness. On only very few occasions have individual ants found their way indoors. These instances occurred during periods of extremely dry weather, and were easily remedied by throwing a little water out on to the ground in or near the places where the dispensers were placed.

A SHORT DESCRIPTION

The invention will be described in more detail below, when reference will be made to the enclosed drawings, which show the preferred design of the invention.

THE PREFERRED DESIGN

Figure 1:
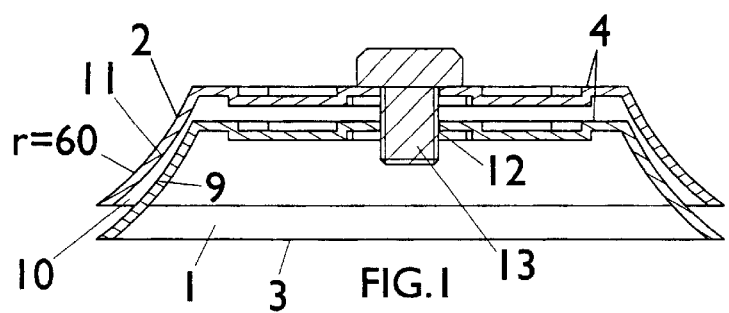
FIG. 1 is a central cross-section of a dispenser.
Figure 2:
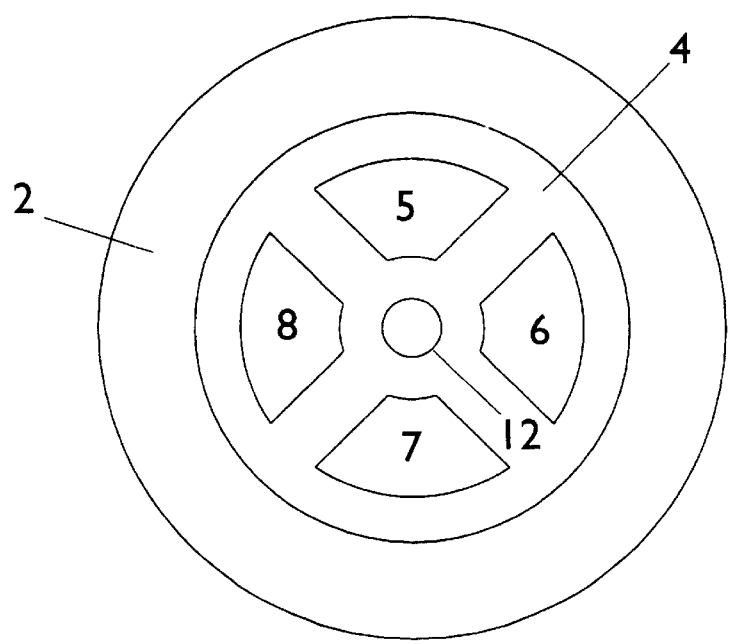
FIG. 2 is a view of the dispenser seen from floor level and below.
Figure 3:
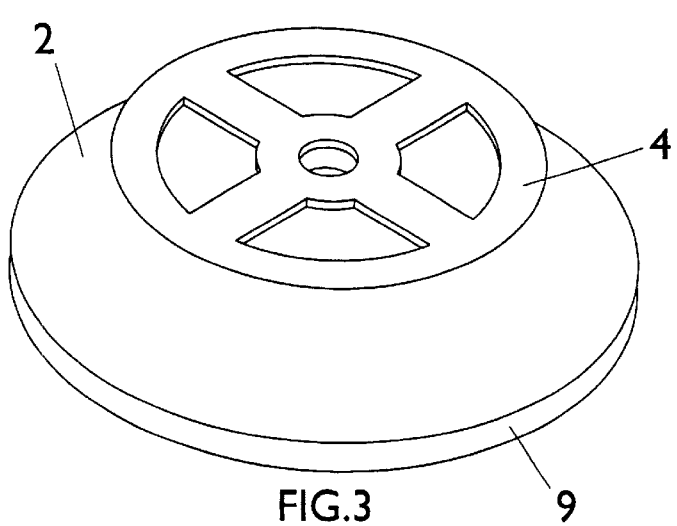
FIG. 3 is a perspective view of the dispenser.

FIG. 1 shows a dispenser, comprising a lower part 1 upon which is fixed an upper part 2 which forms a cover for the dispenser. The lower part 1 is a cut-off cone with slightly concave outer walls. The circular base 3 lies on the ground, so that its upper surface, the cut-off section of the cone, forms a horizontal floor 4, the central portion of which has four depressions 5–8 (see FIG. 2) intended to hold a suitable ant food. The cone's ring-shaped mantle surface 9 forms an upward slope for the ants on their way from the base edge 3 up to the floor section 4.

The roof portion 2, which forms a conical cover, is mounted co-axially upon the lower part 1, so that a ring-shaped channel 10 is formed between the concave, conical outer mantle surface 9 of the lower part, and the roof portion's convex, conical inner mantle surface 11. The depth of the channel is adjustable, as is the space between the floor portion 4 and the roof portion 2, by means of a threaded bolt 13 which passes through threaded holes 12 in the cones 1 and 2. The ants can thus go from the ground upwards along the sloping surface 9 and via the opening 10 to the ant food in the floor portion 4.

Alternatively, the roof portion 2 can be connected to the lower part 1 by means of a snap-on mechanism (not shown).

The most suitable material for the roof portion 2 is a transparent plastic, preferably ultra-violet resistant. The lower part should be of a grey, opaque material, e.g. plastic.

The shape of the body of the dispenser is not important, and it may instead be square, rectangular or rhomboid.

What is claimed is:

1. A method of preventing the entry of ants and termites into a dwelling house, comprising:

luring a colony of ants which are hostile to carpenter ants, Pharaoh ants and termites, to occupy locations close to the dwelling house to be protected, the colony being one already in existence close to said house and that the colony is being lured to the locations by providing food tables with life-sustaining nourishment to the colony of ants in said locations.

2. The method according to claim 1 wherein the method further comprises placing the nourishment inside the food tables so that the nourishment is accessible via openings defined in the food tables.

3. The method according to claim 2 wherein the method further comprises adjusting the openings so that animals that are bigger than the colony of ants cannot pass through the openings.

4. The method according to claim 1 wherein the method further comprises placing the nourishment in a place above a ground surface.

* * * * *